(12) United States Patent
Cotteret

(10) Patent No.: US 7,153,330 B2
(45) Date of Patent: Dec. 26, 2006

(54) COMPOSITION FOR THE OXIDATION DYEING OF KERATIN FIBRES, COMPRISING AT LEAST ONE 4,5- OR 3,4-DIAMINOPYRAZOLE OR A TRIAMINOPYRAZOLE AND AT LEAST ONE SELECTED MINERAL COMPOUND, AND DYEING PROCESS

(75) Inventor: Jean Cotteret, Verneuil sur Seine (FR)

(73) Assignee: L'Oreal (FR)

( * ) Notice: Subject to any disclaimer, the term of this patent is extended or adjusted under 35 U.S.C. 154(b) by 319 days.

(21) Appl. No.: 10/451,552

(22) PCT Filed: Nov. 26, 2001

(86) PCT No.: PCT/FR01/03726

§ 371 (c)(1),
(2), (4) Date: Nov. 25, 2003

(87) PCT Pub. No.: WO02/051371

PCT Pub. Date: Jul. 4, 2002

(65) Prior Publication Data

US 2004/0074014 A1    Apr. 22, 2004

(30) Foreign Application Priority Data

Dec. 22, 2000   (FR) ................... 00 16956

(51) Int. Cl.
*A61K 7/13* (2006.01)

(52) U.S. Cl. .............. 8/405; 8/406; 8/408; 8/522; 8/523; 8/629; 8/632; 8/638; 8/645; 548/372.1; 548/376.1

(58) Field of Classification Search ........... 8/405, 8/406, 522, 523, 629, 632, 637.1, 638, 645, 8/408, 529; 548/372.1, 376.1
See application file for complete search history.

(56) References Cited

U.S. PATENT DOCUMENTS 4,545,978 A * 10/1985 Kalopissis et al. .......... 514/770
5,061,289 A    10/1991 Clausen et al.
6,190,421 B1 *  2/2001 Rondeau et al. ............ 8/407
6,338,741 B1 *  1/2002 Vidal et al. ................ 8/409

FOREIGN PATENT DOCUMENTS

| DE | 38 43 892 | 6/1990 |
|----|-----------|--------|
| DE | 42 08 297 | 9/1993 |
| DE | 42 34 886 | 4/1994 |
| DE | 195 43 988 | 5/1997 |
| DE | 199 51 010 | 4/2001 |
| EP | 0 749 748 | 12/1996 |
| JP | 63-048207 | 2/1988 |
| JP | 04-202119 | 7/1992 |
| JP | 07-502264 | 3/1995 |
| JP | 07-502541 | 3/1995 |
| JP | 07-502542 | 3/1995 |
| JP | 07-502543 | 3/1995 |
| JP | 07-505153 | 6/1995 |
| JP | 08-208448 | 8/1996 |
| JP | 08-239308 | 9/1996 |
| JP | 09-143041 | 6/1997 |
| JP | 10-114635 | 5/1998 |
| JP | 11-246370 | 9/1999 |
| WO | WO-98 22078 | 5/1998 |
| WO | WO-01 34104 | 5/2001 |

OTHER PUBLICATIONS

STIC Search Report dated Aug. 2, 2006.*

* cited by examiner

*Primary Examiner*—Eisa Elhilo
(74) *Attorney, Agent, or Firm*—Lerner, David, Littenberg, Krumholz & Mentlik, LLP

(57) ABSTRACT

The present invention relates to a composition for the oxidation dyeing of keratin fibers, in particular of human keratin fibers such as the hair, comprising at least one oxidation base chosen from 4,5- or 3,4-diaminopyrazoles and triaminopyrazoles, in combination with at least one selected mineral compound, and also to the dyeing process using this composition with an oxidizing agent.

30 Claims, No Drawings

COMPOSITION FOR THE OXIDATION DYEING OF KERATIN FIBRES, COMPRISING AT LEAST ONE 4,5- OR 3,4-DIAMINOPYRAZOLE OR A TRIAMINOPYRAZOLE AND AT LEAST ONE SELECTED MINERAL COMPOUND, AND DYEING PROCESS

The present invention relates to a composition for the oxidation dyeing of keratin fibres, in particular of human keratin fibres such as the hair, comprising at least one oxidation base chosen from 4,5- or 3,4-diaminopyrazoles and triaminopyrazoles, in combination with at least one selected mineral compound, and also to the dyeing process using this composition with an oxidizing agent.

It is known practice to dye keratin fibres, and in particular human hair, with dye compositions containing oxidation dye precursors, in particular ortho- or para-phenylenediamines, ortho- or para-aminophenols or heterocyclic compounds such as pyrazole derivatives which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with suitably selected couplers or coloration modifiers, the latter being chosen in particular from aromatic meta-diamines, meta-aminophenols, meta-diphenols and certain heterocyclic compounds.

The variety of molecules used as regards the oxidation bases and the couplers allows a wide range of colours to be obtained.

The "permanent" coloration obtained by means of these oxidation dyes must moreover satisfy a certain number of requirements. Thus it must not have any toxicological disadvantages, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its end and its root.

Compositions for the oxidation dyeing of keratin fibres, containing pyrazole derivatives such as 4,5-diaminopyrazoles, 3,4-diaminopyrazoles or 3,4,5-triaminopyrazoles as oxidation base have already been proposed, especially in German patent applications DE 3 843 892, DE 4 234 887, DE 4 234 886, DE 4 234 885 or DE 195 43 988. However, such compositions are not entirely satisfactory since, during the dyeing processes, side reactions take place that can have adverse effects in terms of the harmlessness and of the dyeing properties obtained, and especially the strength and resistance of the colorations with respect to the various attacking factors to which the hair may be subjected.

Compositions for the oxidation dyeing of keratin fibres, comprising a combination of an oxidation base of the 4,5-diaminopyrazole type, a zinc salt and a derivative of 1,4-diazacycloheptane or a salt thereof, having the following formula:

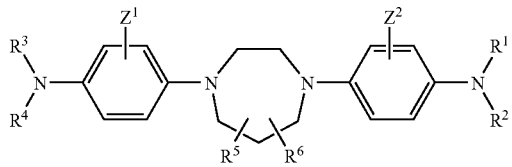

in which $R^1$, $R^2$, $R^3$ and $R^4$, which may be identical or different, denote a hydrogen, a $C_1$–$C_4$ alkyl or hydroxyalkyl, or a $C_2$–$C_4$ dihydroxyalkyl;

$Z^1$ and $Z^2$, which may be identical or different, denote hydrogen, chlorine, fluorine, a $C_1$–$C_4$ alkyl, a $C_1$–$C_4$ hydroxyalkyl, a $C_1$–$C_4$ aminoalkyl, a $C_1$–$C_4$ alkoxy, a $C_2$–$C_4$ dihydroxyalkyl or an allyl group;

$R^5$ and $R^6$, which may be identical or different, denote a hydrogen or a $C_1$–$C_4$ alkyl, are also known in patent application WO 01/34104.

The aim of the invention is to develop novel dye compositions that do not have the drawbacks of the dyes of the prior art, in particular strong dyes that are particularly resistant to the various attacking factors to which the hair may be subjected, and that show good harmlessness.

To this end, one subject of the invention is a composition for the oxidation dyeing of human keratin fibres, and in particular of human keratin fibres such as the hair, comprising, in a medium that is suitable for dyeing:

at least one oxidation base chosen from 4,5- or 3,4-diaminopyrazoles and triaminopyrazoles, and at least one mineral compound chosen from silicas, aluminium oxides or hydroxides, aluminium, magnesium or iron hydrosilicates alone or as a mixture, and zinc salts;

the said composition not containing a combination of an oxidation base of the 4,5-diaminopyrazole type, a zinc salt and a derivative of 1,4-diazacycloheptane or a salt thereof, having the following formula:

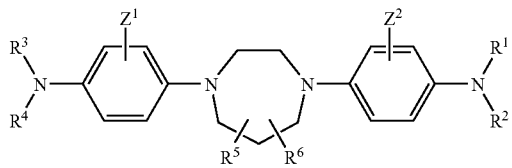

in which $R^1$, $R^2$, $R^3$ and $R^4$, which may be identical or different, denote a hydrogen, a $C_1$–$C_4$ alkyl or hydroxyalkyl, or a $C_2$–$C_4$ dihydroxyalkyl;

$Z^1$ and $Z^2$, which may be identical or different, denote hydrogen, chlorine, fluorine, a $C_1$–$C_4$ alkyl, a $C_1$–$C_4$ hydroxyalkyl, a $C_1$–$C_4$ aminoalkyl, a $C_1$–$C_4$ alkoxy, a $C_2$–$C_4$ dihydroxyalkyl or an allyl group;

$R^5$ and $R^6$, which may be identical or different, denote a hydrogen or a $C_1$–$C_4$ alkyl.

The oxidation dye composition of the invention makes it possible to obtain, with good harmlessness, strong, relatively unselective colorations in varied shades, which show excellent resistance properties both with respect to atmospheric agents such as light and bad weather and with respect to perspiration and various treatments to which the hair may be subjected (shampooing or permanent reshaping).

Except where otherwise mentioned, all the radicals, substituents, groups and chains in the context of the invention are linear or branched, and substituted or unsubstituted.

Among the silicas that are useful in the composition of the invention, mention may be made of crystalline, microcrystalline and non-crystalline silicas.

By way of example, crystalline silicas that may be mentioned include quartz, tridymite, cristobalite, keatite, coesite and stishovite. The microcrystalline silicas are, for example, diatomite.

Among the non-crystalline forms that may be used are vitreous silica and other types of amorphous silicas such as colloidal silicas, silica gels, precipitated silicas and fumed silicas, for instance aerosils, and pyrogenic silicas.

Among the aluminium hydroxides that may be used according to the invention, mention may be made of compounds having the composition Al(OH)$_3$, such as the α-alumina trihydrate hydragillite or gibbsite or the β-alumina trihydrate bayerite, and compounds having the composition AlOOH, such as the new β-trihydrate nordstrandite, the α-alumina monohydrate boehmite and the β-alumina monohydrate diaspore.

Among the aluminium oxides that may be used according to the invention, mention may be made of activated aluminas whose crystal structure is that of the γ, η, χ or ρ transition aluminas, or the calcined aluminas such as α alumina. Mention may also be made of β aluminas such as sodium β-aluminates, sodium γ-aluminates, sodium β-aluminas, potassium β-aluminas, magnesium β-aluminas, calcium β-aluminas, strontium β-aluminas, barium β-aluminas and lithium ξ-aluminas.

Among the aluminium hydrosilicates that may be mentioned are kaolinite, dicktite, nacrite and halloysite-endellite found in clays of kaolin type, and also pyrophyllite and beidellite found in smectites.

Among the magnesium hydrosilicates that may be mentioned are talc, which is found in smectites, and serpentines such as chrysotile.

Among the hydrosilicates containing several of the above metal elements, mention may be made of montmorillonite and saponite (aluminium+magnesium), nontronite (aluminium+iron) and sauconite (aluminium+magnesium+iron) which are found in smectites, and amesite (aluminium+magnesium), chamosite and illite (iron+aluminium+magnesium).

Among the zinc salts that may be mentioned are the salts obtained with a mineral acid, for instance the sulphate, hydrochloride, nitrate, carbonate, hydrogen carbonate, orthophosphate, ortho-hydrogen phosphate and ortho-dihydrogen phosphate, and the salts obtained with organic acids, for instance the tartrate, citrate, acetate or lactate.

The mineral compound(s) preferably represent(s) from 0.00001% to 10% by weight and even more preferably from 0.001% to 5% by weight approximately relative to the total weight of the dye composition, and even more preferentially from 0.001% to 3% by weight approximately relative to this weight.

Among the 4,5- or 3,4-diaminopyrazoles that are useful in the dye compositions of the invention, mention may be made particularly of the diaminopyrazoles chosen from the 4,5- or 3,4-diaminopyrazoles of formula (I) or (II) below, and/or the addition salts thereof with an acid:

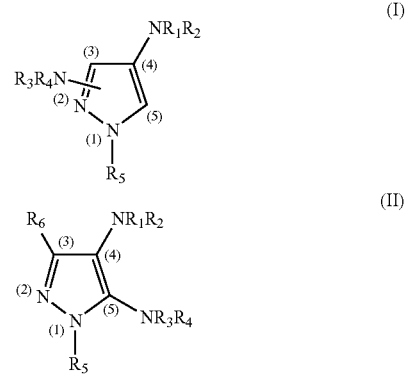

in which:
$R_1$, $R_2$, $R_3$, $R_4$ and $R_5$, which may be identical or different, represent a hydrogen atom; a $C_1$–$C_6$ alkyl radical which is unsubstituted or substituted with at least one substituent chosen from OR, NHR, NRR', SR, SOR, SO$_2$R, COR, COOH, CONH$_2$, CONHR, CONRR', PO(OH)$_2$, SH and SO$_3$X, a non-cationic heterocycle, Cl, Br or I, X denoting a hydrogen atom, Na, K or NH$_4$, and R and R', which may be identical or different, representing a $C_1$–$C_4$ alkyl or alkenyl; a $C_2$–$C_4$ hydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; a radical

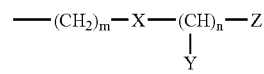

in which m and n are integers, which may be identical or different, between 0 and 3 inclusive, X represents an oxygen atom or an NH group, Y represents a hydrogen atom or a $C_1$–$C_4$ alkyl radical, and Z represents a methyl radical when n is equal to 0, or Z represents a $C_1$–$C_4$ alkyl radical, a group OR or NR"R'" when n is greater than or equal to 1, R" and R'", which may be identical or different, denoting a hydrogen atom or a $C_1$–$C_4$ alkyl radical; or $R_9$ forms with the nitrogen atom of the group NR$_7$R$_8$ in position 5 an at least 4-membered heterocycle, $R_6$ represents a $C_1$–$C_6$ alkyl radical; a $C_1$–$C_4$ hydroxyalkyl radical; a $C_1$–$C_4$ aminoalkyl radical; a ($C_1$–$C_4$)alkylamino ($C_1$–$C_4$)alkyl radical; a di($C_1$–$C_4$)alkylamino($C_1$–$C_4$) alkyl radical; a hydroxy($C_1$–$C_4$)alkylamino($C_1$–$C_4$)alkyl radical; a ($C_1$–$C_4$)alkoxymethyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle chosen from thiophene, furan and pyridine, or a radical —(CH$_2$)$_p$— O—(CH$_2$)$_q$—OR", in which p and q are integers, which may be identical or different, between 1 and 3 inclusive and R" is as defined above, it being understood that:

at least one of the radicals $R_1$, $R_2$, $R_3$ and $R_4$ represents a hydrogen atom.

Among the triaminopyrazoles that are useful as oxidation bases in the dye compositions in accordance with the invention, mention may be made more particularly of the compounds of formula (III) below, and the addition salts thereof with an acid:

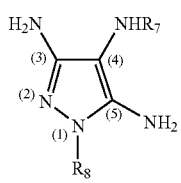

in which:
R_7 and R_8, which may be identical or different, represent a hydrogen atom or a $C_1$–$C_4$ alkyl or $C_2$–$C_4$ hydroxyalkyl radical.

Among the 4,5- or 3,4-diaminopyrazoles of formula (I) above that may be mentioned more particularly are 4,5-diamino-1-(4'-methoxybenzyl)pyrazole, 4,5-diamino-1-(4'-methylbenzyl)pyrazole, 4,5-diamino-1-(4'-chlorobenzyl)pyrazole, 4,5-diamino-1-(3'-methoxybenzyl)pyrazole, 4-amino-1-(4'-methoxybenzyl)-5-methylaminopyrazole, 4-amino-5-(β-hydroxyethyl)amino-1-(4'-methoxybenzyl)pyrazole, 4-amino-5-(β-hydroxyethyl)amino-1-methylpyrazole, 4-amino-(3)-5-methylaminopyrazole, 3-(5),4-diaminopyrazole, 4,5-diamino-1-methylpyrazole, 4,5-diamino-1-ethylpyrazole, 4,5-diamino-1-isopropylpyrazole, 4,5-diamino-1-hydroxyethylpyrazole, 4,5-diamino-1-benzylpyrazole, 4-diamino-5-hydroxyethylamino-1-hydroxyethylpyrazole, 4-diamino-5-methylamino-1-hydroxyethylpyrazole, 3-amino-4,5,7,8-tetrahydropyrazolo[1,5-a]pyrimidine, 7-amino-2,3-dihydro-1H-imidazole[1,2-b]pyrazole, 3-amino-8-methyl-4,5,7,8-tetrahydropyrazolo[1,5-a]-pyrimidine, 2-(4,5-diamino-1-pyrazolyl)-1-ethanesulphonic acid, 2-(4,5-diamino-1-pyrazolyl)acetamide, 2-(4,5-diamino-1-pyrazolyl)acetic acid, 2-(2-dimethylaminoethyl)-2H-pyrazole-3,4-diamine and 2-(2-methoxyethyl)-2H-pyrazole-3,4-diamine, and the addition salts thereof with an acid.

The diaminopyrazoles that are useful in the present invention may be obtained via synthetic processes that are well known to those skilled in the art. For example, the 4,5-diaminopyrazoles of formula (II) may be prepared according to the synthetic process as described, for example, in French patent application FR-A-2 733 749.

Among the 4,5-diaminopyrazoles of formula (II) above that may be mentioned more particularly are:
1-benzyl-4,5-diamino-3-methylpyrazole,
4,5-diamino-1-(β-hydroxyethyl)-3-(4'-methoxyphenyl)pyrazole,
4,5-diamino-1-(β-hydroxyethyl)-3-(4'-methylphenyl)pyrazole,
4,5-diamino-1-(β-hydroxyethyl)-3-(3'-methylphenyl)pyrazole,
4,5-diamino-3-methyl-1-isopropylpyrazole,
4,5-diamino-3-(4'-methoxyphenyl)-1-isopropylpyrazole,
4,5-diamino-1-ethyl-3-methylpyrazole,
4,5-diamino-1-ethyl-3-(4'-methoxyphenyl)pyrazole,
4,5-diamino-3-hydroxymethyl-1-methylpyrazole,
4,5-diamino-1-ethyl-3-hydroxymethylpyrazole,
4,5-diamino-3-hydroxymethyl-1-isopropylpyrazole,
4,5-diamino-3-hydroxymethyl-1-tert-butylpyrazole,
4,5-diamino-3-hydroxymethyl-1-phenylpyrazole,
4,5-diamino-3-hydroxymethyl-1-(2'-methoxyphenyl)pyrazole,
4,5-diamino-3-hydroxymethyl-1-(3'-methoxyphenyl)pyrazole,
4,5-diamino-3-hydroxymethyl-1-(4'-methoxyphenyl)pyrazole,
1-benzyl-4,5-diamino-3-hydroxymethylpyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-ethylpyrazole,
4,5-diamino-3-dimethylaminomethyl-1-isopropylpyrazole,
4,5-diamino-3-dimethylaminomethyl-1-tert-butylpyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethylpyrazole,
4,5-diamino-3-[(β-hydroxyethyl)aminomethyl]-1-methylpyrazole,
4,5-diamino-3-[(β-hydroxyethyl)aminomethyl]-1-isopropylpyrazole,
4,5-diamino-1-ethyl-3-[(β-hydroxyethyl)aminomethyl]pyrazole,
1-tert-butyl-4,5-diamino-3-[(β-hydroxyethyl)aminomethyl]pyrazole,
4-amino-5-(β-hydroxyethyl)amino-1,3-dimethylpyrazole,
4-amino-5-(β-hydroxyethyl)amino-1-isopropyl-3-methylpyrazole,
4-amino-5-(β-hydroxyethyl)amino-1-ethyl-3-methylpyrazole,
4-amino-5-(β-hydroxyethyl)amino-1-tert-butyl-3-methylpyrazole,
4-amino-5-(β-hydroxyethyl)amino-1-phenyl-3-methylpyrazole,
4-amino-5-(β-hydroxyethyl)amino-1-(2-methoxyphenyl)-3-methylpyrazole,
4-amino-5-(β-hydroxyethyl)amino-1-(3-methoxyphenyl)-3-methylpyrazole,
4-amino-5-(β-hydroxyethyl)amino-1-(4-methoxyphenyl)-3-methylpyrazole,
4-amino-5-(β-hydroxyethyl)amino-1-benzyl-3-methylpyrazole,
4-amino-1-ethyl-3-methyl-5-methylaminopyrazole,
4-amino-1-tert-butyl-3-methyl-5-methylaminopyrazole,
4,5-diamino-1,3-dimethylpyrazole,
4,5-diamino-3-tert-butyl-1-methylpyrazole,
4,5-diamino-1-tert-butyl-3-methylpyrazole,
4,5-diamino-1-methyl-3-phenylpyrazole,
4,5-diamino-1-(β-hydroxyethyl)-3-methylpyrazole,
4,5-diamino-1-(β-hydroxyethyl)-3-phenylpyrazole,
4,5-diamino-1-methyl-3-(2'-chlorophenyl)pyrazole,
4,5-diamino-1-methyl-3-(4'-chlorophenyl)pyrazole,
4,5-diamino-1-methyl-3-(3'-trifluoromethylphenyl)pyrazole,
4,5-diamino-1,3-diphenylpyrazole,
4,5-diamino-3-methyl-1-phenylpyrazole,
4-amino-1,3-dimethyl-5-phenylaminopyrazole, 4-amino-1-ethyl-3-methyl-5-phenylaminopyrazole,
4-amino-1,3-dimethyl-5-methylaminopyrazole,
4-amino-3-methyl-1-isopropyl-5-methylaminopyrazole,
4-amino-3-isobutoxymethyl-1-methyl-5-methylaminopyrazole,
4-amino-3-methoxyethoxymethyl-1-methyl-5-methylaminopyrazole,
4-amino-3-hydroxymethyl-1-methyl-5-methylaminopyrazole,
4-amino-1,3-diphenyl-5-phenylaminopyrazole,
4-amino-3-methyl-5-methylamino-1-phenylpyrazole,
4-amino-1,3-dimethyl-5-hydrazinopyrazole,
5-amino-3-methyl-4-methylamino-1-phenylpyrazole,
5-amino-1-methyl-4-(N,N-methylphenyl)amino-3-(4'-chlorophenyl)pyrazole,
5-amino-3-ethyl-1-methyl-4-(N,N-methylphenyl)aminopyrazole,
5-amino-1-methyl-4-(N,N-methylphenyl)amino-3-phenylpyrazole,
5-amino-3-ethyl-4-(N,N-methylphenyl)aminopyrazole,
5-amino-4-(N,N-methylphenyl)amino-3-phenylpyrazole,
5-amino-4-(N,N-methylphenyl)amino-3-(4'-methylphenyl)pyrazole,
5-amino-3-(4'-chlorophenyl)-4-(N,N-methylphenyl)aminopyrazole,
5-amino-3-(4'-methoxyphenyl)-4-(N,N-methylphenyl)aminopyrazole,
4-amino-5-methylamino-3-phenylpyrazole,
4-amino-5-ethylamino-3-phenylpyrazole,
4-amino-5-ethylamino-3-(4'-methylphenyl)pyrazole,
4-amino-3-phenyl-5-propylaminopyrazole,
4-amino-5-butylamino-3-phenylpyrazole,
4-amino-3-phenyl-5-phenylaminopyrazole,
4-amino-5-benzylamino-3-phenylpyrazole,
4-amino-5-(4'-chlorophenyl)amino-3-phenylpyrazole,
4-amino-3-(4'-chlorophenyl)-5-phenylaminopyrazole,
4-amino-3-(4'-methoxyphenyl)-5-phenylaminopyrazole,
1-(4'-chlorobenzyl)-4,5-diamino-3-methylpyrazole,
4,5-diamino-3-hydroxymethyl-1-isopropylpyrazole,
4-amino-1-ethyl-3-methyl-5-methylaminopyrazole,
4-amino-5-(2'-aminoethyl)amino-1,3-dimethylpyrazole, and the addition salts thereof with an acid.

Among the 4,5- or 3,4-diaminopyrazoles of formula (I) above, the following are more particularly preferred:
4,5-diamino-1-benzylpyrazole,
4,5-diamino-1-(4'-chlorobenzyl)pyrazole,
4,5-diamino-1-methylpyrazole,
4,5-diamino-1-hydroxyethylpyrazole,
2-(2-methoxyethyl)-2H-pyrazole-3,4-diamine and the addition salts thereof with an acid.

Among the 4,5-diaminopyrazoles of formula (II) above, the following are more particularly preferred:
4,5-diamino-1,3-dimethylpyrazole,
4,5-diamino-3-methyl-1-phenylpyrazole,
4,5-diamino-1-methyl-3-phenylpyrazole,
4-amino-1,3-dimethyl-5-hydrazinopyrazole,
1-benzyl-4,5-diamino-3-methylpyrazole,
4,5-diamino-3-tert-butyl-1-methylpyrazole,
4,5-diamino-1-tert-butyl-3-methylpyrazole,
4,5-diamino-1-(β-hydroxyethyl)-3-methylpyrazole,
4,5-diamino-1-ethyl-3-methylpyrazole,
4,5-diamino-1-ethyl-3-(4'-methoxyphenyl)pyrazole,
4,5-diamino-1-ethyl-3-hydroxymethylpyrazole,
4,5-diamino-3-hydroxymethyl-1-methylpyrazole,
4,5-diamino-3-hydroxymethyl-1-isopropylpyrazole,
4,5-diamino-3-methyl-1-isopropylpyrazole,
4-amino-5-(2'-aminoethyl)amino-1,3-dimethylpyrazole, and the addition salts thereof with an acid.

Among the triaminopyrazoles of formula (III) above that may be mentioned more particularly are 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the additions salts thereof with an acid.

The 4,5- or 3,4-diaminopyrazole(s) and/or the triaminopyrazole(s) in accordance with the invention and/or the corresponding addition salt(s) with an acid preferably represent from 0.0005% to 12% by weight approximately relative to the total weight of the dye composition and more preferably from 0.005% to 6% by weight approximately relative to this weight.

Preferably, the weight ratio of the mineral compound(s) to the 4,5- or 3,4-diaminopyrazole(s) and/or the triaminopyrazole(s) and/or the addition salt(s) with an acid is between 0.001 and 100 and even more preferably between 0.01 and 10.

The dye compositions in accordance with the invention preferably contain at least one coupler. The couplers that may be used are those conventionally used for oxidation dyeing, and especially meta-phenylenediamines, meta-aminophenols, meta-diphenols, naphthol derivatives and heterocyclic couplers.

The meta-phenylenediamines, meta-aminophenols and meta-diphenols which may be used as additional couplers in the dye composition in accordance with the invention are preferably chosen from the compounds corresponding to formula (1) below, and the addition salts thereof with an acid:

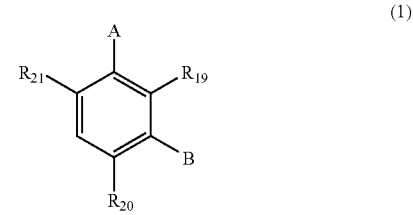

in which:

A and B, which may be identical or different, represent a hydroxyl, amino or —$NHR_{22}$ radical in which $R_{22}$ represents a $C_1$–$C_4$ alkyl, $C_1$–$C_4$ monohydroxyalkyl or $C_2$–$C_4$ polyhydroxyalkyl radical, $R_{19}$, $R_{20}$ and $R_{21}$, which may be identical or different, represent a hydrogen atom or a halogen atom such as a bromine, chlorine, iodine or fluorine atom, or a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkoxy radical.

Among the compounds of formula (1) above, mention may be made in particular of 2-methyl-5-aminophenol, 2-methyl-5-amino-6-chlorophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene and 2,6-bis(β-hydroxyethylamino)toluene, and the addition salts thereof with an acid.

The heterocyclic coupler(s) which may be used as additional couplers in the dye composition in accordance with the invention can be chosen in particular from indole derivatives, indoline derivatives, pyridine derivatives, pyrimidine derivatives and pyrazolones, and the addition salts thereof with an acid.

Among these heterocyclic couplers, mention may be made in particular, for example, of sesamol, 1-N-(β-hydroxyethyl)amino-3',4-methylenedioxybenzene, 6-hydroxyindole, 4-hydroxyindole, 4-hydroxy-N-methylindole, 6-hydroxyindoline, 6-hydroxybenzomorpholine, 2,6-dihydroxy-4-methylpyridine, 3,5-diamino-2,6-dimethoxypyridine, 2-amino-3-hydroxypyridine, 1-H-3-methylpyrazol-5-one and 1-phenyl-3-methylpyrazol-5-one, and the addition salts thereof with an acid.

Among the naphthol derivatives that may be mentioned are α-naphthol and 2-methyl-1-naphthol.

The additional coupler(s) preferably represent(s) from 0.0001% to 10% by weight approximately relative to the total weight of the dye composition, and even more preferably from 0.005% to 5% by weight approximately relative to this weight.

The dye compositions in accordance with the invention may also contain other oxidation bases conventionally used for oxidation dyeing, other than a diaminopyrazole and a triaminopyrazole and/or direct dyes, especially to modify the shades or to enrich them with glints.

The additional oxidation bases that may be used in the context of the present invention are chosen from those conventionally known in oxidation dyeing, and among which mention may be made especially of ortho- and para-phenylenediamines, double bases, ortho- and para-aminophenols, and heterocyclic bases other than the pyrazoles of the invention, and also the addition salts thereof with an acid, and especially:

(I) the para-phenylenediamines of formula (2) below, and the addition salts thereof with an acid:

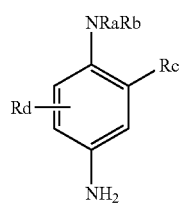

(2)

in which:
$R_a$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ alkyl radical substituted with a nitrogenous group, a phenyl radical or a 4'-aminophenyl radical;
$R_b$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;
$R_c$ represents a hydrogen atom, a halogen atom such as a chlorine atom, a $C_1$–$C_4$ alkyl radical, a sulfo radical, a carboxyl radical, a $C_1$–$C_4$ monohydroxyalkyl radical, a $C_1$–$C_4$ hydroxyalkoxy radical, an acetylamino$(C_1$–$C_4)$ alkoxy radical, a $C_1$–$C_4$ mesylaminoalkoxy radical or a carbamoylamino$(C_1$–$C_4)$alkoxy radical,
$R_d$ represents a hydrogen or halogen atom or a $C_1$–$C_4$ alkyl radical,
$R_a$ and $R_b$ may also form with the nitrogen atom that bears them a 5- or 6-membered nitrogenous heterocycle optionally substituted with one or more alkyl, hydroxyl or ureido groups.

Among the nitrogenous groups of formula (2) above, mention may be made in particular of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the para-phenylenediamines of formula (2) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the addition salts thereof with an acid.

Among the para-phenylenediamines of formula (2) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid are most particularly preferred.

(II) the double bases are compounds comprising at least two aromatic nuclei bearing amino and/or hydroxyl groups.

Among the double bases which can be used as oxidation bases in the dye compositions in accordance with the invention, mention may be made in particular of the compounds corresponding to formula (3) below, and the addition salts thereof with an acid:

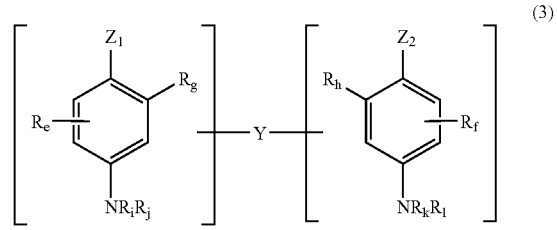

(3)

in which:
$Z_1$ and $Z_2$, which may be identical or different, represent a hydroxyl or —$NH_2$ radical which may be substituted with a $C_1$–$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;

$R_e$ and $R_f$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;

$R_g$, $R_h$, $R_i$, $R_j$, $R_k$ and $R_l$, which may be identical or different, represent a hydrogen atom, a linker arm Y or a $C_1$–$C_4$ alkyl radical;

it being understood that the compounds of formula (3) contain only one linker arm Y per molecule.

Among the nitrogenous groups of formula (3) above, mention may be made in particular of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (3) above, mention may be made more particularly of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl), N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid. Among these double bases of formula (3), N,N'-bis(β-hydroxyethyl)-N,N'-bis(4'-aminophenyl)-1,3-diamino-propanol and 1,8-bis(2,5-diaminophenoxy)-3,6-dioxaoctane, or one of the addition salts thereof with an acid, are particularly preferred.

(III) the para-aminophenols corresponding to formula (4) below, and the addition salts thereof with an acid:

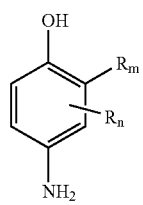

(4)

in which:

$R_m$ represents a hydrogen or halogen atom such as fluorine or a $C_1$–$C_4$ alkyl, $C_1$–$C_4$ monohydroxyalkyl, ($C_1$–$C_4$)alkoxy($C_1$–$C_4$)alkyl, $C_1$–$C_4$ aminoalkyl or hydroxy($C_1$–$C_4$)alkylamino($C_1$–$C_4$)alkyl radical, $R_n$ represents a hydrogen or halogen atom such as fluorine or a $C_1$–$C_4$-alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy-($C_1$–$C_4$)alkyl radical.

Among the para-aminophenols of formula (4) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

(IV) the ortho-aminophenols that may be used as oxidation bases in the context of the present invention are chosen especially from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) among the heterocyclic bases which can be used as oxidation bases in the dye compositions in accordance with the invention, mention may be made more particularly of pyridine derivatives, pyrimidine derivatives and pyrazole derivatives and the addition salts thereof with an acid.

Among the pyridine derivatives, mention may be made more particularly of the compounds described, for example, in patents GB 1,026,978 and GB 1,153,196, such as-2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in patents DE 2 359 399; JP 88-169 571; JP 91-10659 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]-pyrimidine-3,5-diamine, 2,7-dimethylpyrazolo[1,5-a]-pyrimidine-3,5-diamine, 3-aminopyrazolo[1,5-a]-pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]-pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, the addition salts thereof, and the tautomeric forms thereof, when a tautomeric equilibrium exists, and the addition salts thereof with an acid.

According to the present invention, the additional oxidation bases may preferably represent from 0.0005% to 12% by weight approximately relative to the total weight of the dye composition.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for the dyeing (or the support) generally consists of water or of a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately and preferably between 5 and 11 approximately. It may be adjusted to the desired value with the aid of acidifying or basifying agents commonly used in the dyeing of keratin fibres.

Among the acidifying agents, mention may be made, by way of example, of inorganic or organic acids such as hydrochloric acid, orthophosphoric acid, carboxylic acids such as tartaric acid, citric acid or lactic acid, and sulphonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (5) below:

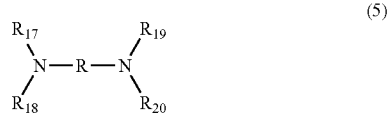
(5)

in which R is a propylene residue optionally substituted with a hydroxyl group or a $C_1$–$C_4$ alkyl radical; $R_{17}$, $R_{18}$, $R_{19}$ and $R_{20}$, which may be identical or different, represent a hydrogen atom or a $C_1$–$C_4$ alkyl or $C_1$–$C_4$ hydroxyalkyl radical.

The dye composition in accordance with the invention can also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners, such as, for example, volatile or non-volatile silicones, which are modified or unmodified, film-forming agents, ceramides, preserving agents and opacifiers.

Needless to say, a person skilled in the art will take care to select this or these optional complementary compound(s) such that the advantageous properties intrinsically associated with the combination in accordance with the invention is (are) not, or not substantially, adversely affected by the addition or additions envisaged.

The dye composition in accordance with the invention can be in various forms, such as in the form of liquids, creams or gels or in any other form that is suitable for dyeing keratin fibres, and especially human hair.

A subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent, this oxidizing agent possibly being added just at the time of use to the dye composition or by means of an oxidizing composition applied simultaneously or sequentially.

According to one particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left to stand on them for about 3 to 60 minutes, preferably about 5 to 40 minutes, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates, persalts such as perborates, percarbonates and persulphates, and peracids. Hydrogen peroxide is particularly preferred.

The pH of the oxidizing composition containing the oxidizing agent as defined above is such that, after mixing it with the dye composition, the pH of the resulting composition applied to the keratin fibres preferably ranges between about 3 and 12 and even more preferably between 5 and 11. It is adjusted to the desired value by means of acidifying or basifying agents usually used for the dyeing of keratin fibres and as defined above.

The oxidizing composition as defined above can also contain various adjuvants conventionally used in compositions for dyeing the hair and as defined above.

The dye composition that is applied to the keratin fibres can be in various forms, such as in the form of liquids, creams or gels or any other form which is suitable for dyeing keratin fibres, and in particular human hair.

According to one variant, a composition containing at least the mineral compound is applied to these fibres in a first stage, and a composition containing at least one diaminopyrazole is applied in a second stage, the application of the composition containing the mineral compound(s) possibly being followed by a rinsing step, the colour being developed using an oxidizing agent.

Another subject of the invention is a multi-compartment device or dyeing "kit" or any other multi-compartment packaging system, a first compartment of which contains the dye composition as defined above and a second compartment of which contains the oxidizing composition as defined above. These devices may be equipped with a means for applying the desired mixture to the hair, such as the devices described in patent FR-2 586 913 in the name of the Applicant.

According to a different embodiment, the device comprises at least three compartments, a first compartment that contains the mineral compound that is useful for the invention, a second compartment that contains a diaminopyrazole, and a third compartment that contains an oxidizing composition.

The examples that follow are intended to illustrate the invention without, however, limiting its scope.

EXAMPLES

Dyeing Examples 1 to 4

The dye compositions below, in accordance with the invention, were prepared (amounts in grams, AM denotes Active Material):

|  | EXAMPLES | | | |
| --- | --- | --- | --- | --- |
|  | 1 | 2 | 3 | 4 |
| 4,5-Diamino-1β-hydroxyethyl-pyrazole dihydrochloride (oxidation base) | 0.645 | 0.645 | 0.645 | 0.645 |

-continued

| | | | | |
|---|---|---|---|---|
| 3-Amino-6-methylphenol (coupler) | 0.369 | 0.369 | 0.369 | 0.369 |
| Amorphous pyrogenic silica sold under the name Acematt TS 100 by the company Degussa-Hüls (mineral compound according to the invention) | 0.3 | — | — | — |
| Alumina of small particle size sold under the name AluminiumoxidC by the company Degussa-Hüls (mineral compound according to the invention) | — | 0.2 | — | — |
| Boehmite as a 75% colloidal suspension sold under the name Dispersal S by the company Condea (mineral compound according to the invention) | — | — | 0.15 AM | — |
| Zinc sulphate containing 7 molecules of water (mineral compound according to the invention) | — | — | — | 0.8 |
| Common dye support | () | () | () | () |
| Demineralized water qs | 100 g | 100 g | 100 g | 100 g |

(**) common dye support containing:

| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 by the company Akzo | 7.0 g |
| Diethylaminopropyl laurylamino-succinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% NH$_3$ | 10 g |

At the time of use, each dye composition above was mixed with an equal amount by weight of an oxidizing composition consisting of a 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

In all cases, a strong and resistant red shade, with good harmlessness, is obtained.

Dyeing Examples 5 to 7

The dye compositions below, in accordance with the invention, were prepared (amounts in grams):

| | EXAMPLE | | |
|---|---|---|---|
| | 5 | 6 | 7 |
| 4,5-Diamino-1-ethyl-3-methyl-pyrazole dihydrochloride (oxidation base) | 0.639 | 0.639 | — |

-continued

| | EXAMPLE | | |
|---|---|---|---|
| | 5 | 6 | 7 |
| 3,4,5-Triaminopyrazole dihydrochloride (oxidation base) | — | — | 0.667 |
| 3-Amino-6-methylphenol (coupler) | 0.369 | 0.369 | 0.369 |
| Boehmite as a 75% colloidal suspension, sold under the name Dispersal S by the company Condea (mineral compound according to the invention) | 0.15 AM | — | 0.15 AM |
| Zinc sulphate containing 7 molecules of water (mineral compound according to the invention) | — | 0.2 | — |
| Common dye support | () | () | (**) |
| Demineralized water qs | 100 g | 100 g | 100 g |

(**) common dye support: identical to that of Examples 1 to 4.

At the time of use, each dye composition above was mixed with an equal amount by weight of an oxidizing composition consisting of a 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

In the three cases, a strong and resistant shade, with good harmlessness, is obtained.

What is claimed is:

1. Composition for the oxidation dyeing of human keratin fibres, and in particular of human keratin fibres such as the hair, comprising, in a medium that is suitable for dyeing:
   4,5-diamino 1-hydroxyethyl pyrazole, and/or the addition salt thereof with an acid and
   at least one mineral compound chosen from silicas, aluminium oxides or hydroxides, aluminium, magnesium and iron hydrosilicates alone or as a mixture, and zinc salts; the said composition not containing a combination of an oxidation base of the 4,5-diaminopyrazole type, a zinc salt and a derivative of 1,4-diazacycloheptane or a salt thereof, having the following formula:

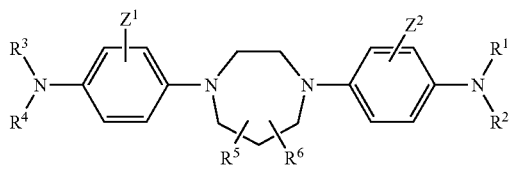

in which $R^1$, $R^2$, $R^3$ and $R^4$, which may be identical or different, denote a hydrogen, a $C_1$–$C_4$ alkyl or hydroxyalkyl, or a $C_2$–$C_4$ dihydroxyalkyl;
$Z^1$ and $Z^2$, which may be identical or different, denote hydrogen, chlorine, fluorine, a $C_1$–$C_4$ alkyl, a $C_1$–$C_4$ hydroxyalkyl, a $C_1$–$C_4$ aminoalkyl, a $C_1$–$C_4$ alkoxy, a $C_2$–$C_4$ dihydroxyalkyl or an allyl group;
$R^5$ and $R^6$, which may be identical or different, denote a hydrogen or a $C_1$–$C_4$ alkyl.

2. Composition according to claim 1, characterized in that the silica(s) is(are) chosen from crystalline or microcrystalline silicas and non-crystalline silicas.

3. Composition according to claim 2, characterized in that the non-crystalline silica is vitreous silica.

4. Composition according to claim 2, characterized in that the non-crystalline silica is chosen from amorphous silicas such as colloidal silicas, silica gels, precipitated silicas and fumed silicas.

5. Composition according to claim 1, characterized in that the aluminium hydroxides are chosen from the compounds of composition Al (OH)$_3$ and the compounds of composition AlOOH.

6. Composition according to claim 1, characterized in that the aluminium oxides are chosen from activated aluminas and calcined aluminas.

7. Composition according to claim 6, characterized in that the activated alumina is α alumina.

8. Composition according to claim 1, characterized in that the hydrosilicates are chosen from kaolinite, dicktite, nacrite, halloysite-endellite, pyrophyllite, beidellite, talc, chrysotile, montmorillonite, saponite, nontronite, sauconite, amesite, chamosite and illite.

9. Composition according to claim 1, characterized in that the zinc salts are chosen from the salts obtained with a mineral acid.

10. Composition according to claim 9, characterized in that the zinc salts are chosen from zinc chloride, sulphate, nitrate, orthophosphate, ortho-hydrogen phosphate, ortho-dihydrogen phosphate, carbonate and hydrogen carbonate.

11. Composition according to claim 1, characterized in that the zinc salts are chosen from the salts obtained with an organic acid.

12. Composition according to claim 1, characterized in that the mineral compound(s) represent(s) from 0.00001% to 10% by weight approximately relative to the total weight of the dye composition.

13. The composition of claim 1, wherein said 4,5-diamino 1-hydroxyethyl pyrazole and/or the corresponding addition salt(s) with an acid represent from 0.0005% to 12% by weight relative to the total weight of the dye composition.

14. The composition of claim 13, wherein said 4,5-diamino 1-hydroxyethyl pyrazole and/or the corresponding addition salt(s) with an acid represent from 0.005% to 6% by weight relative to the total weight of the dye composition.

15. The composition of claim 1, wherein that the weight ratio of the mineral compound(s) to the 4,5-diamino 1-hydroxyethyl pyrazole and/or the addition salt(s) with an acid is between 0.001 and 100.

16. The composition of claim 1, wherein said addition salts with an acid are selected from the group consisting of hydrochlorides, hydrobromides, sulphates, tartrates, lactates and acetates.

17. The composition of claim 1, further comprising at least one coupler.

18. The composition of claim 17, wherein said coupler(s) represent(s) from 0.0001% to 10% by weight approximately relative to the total weight of the dye composition.

19. The composition of claim 1, further comprising at least one additional oxidation base other than the pyrazoles defined in claims 1 to 12.

20. The composition of claim 19, wherein said additional oxidation base(s) represent(s) from 0.0005% to 12% by weight approximately relative to the total weight of the dye composition.

21. The composition of claim 1, wherein it has a pH of between 3 and 12.

22. The composition of claim 1, wherein it is in the form of liquids, creams or gels or in any other form that is suitable for dyeing keratin fibres, and especially human hair.

23. Process for dyeing keratin fibres, and in particular human keratin fibres such as the hair, comprising the step of applying the composition of claim 1 to said fibres, and wherein the colour is revealed at acidic, neutral or alkaline pH using an oxidizing agent.

24. The process of claim 23, wherein said oxidizing agent is chosen from hydrogen peroxide, urea peroxide, alkali metal bromates, persalts such as perborates, percarbonates and persulphates, and peracids.

25. A process for dyeing keratin fibres, and in particular human keratin fibres such as the hair, comprising the steps of applying to said fibres a composition containing at least one mineral compound as defined in claim 1 in a first stage, applying to said fibres a composition containing said 4,5-diamino 1-hydroxyethyl pyrazole as defined in claim 1 in a second stage, the application of said composition containing said mineral compound(s) possibly being followed by a rinsing step, and wherein the colour is developed using an oxidizing agent.

26. A multi-compartment device comprising a first compartment containing said dye composition of claim 1 and a second compartment containing an oxidizing composition.

27. A multi-compartment device comprising a first compartment containing said mineral compound as defined in claim 1, a second compartment containing said 4,5-diamino 1-hydroxyethyl pyrazole as defined in claim 1, and a third compartment containing an oxidizing composition.

28. The composition of claim 12 wherein the mineral compound(s) represent(s) from 0.001% to 5% by weight approximately relative to the total weight of the dye composition.

29. The composition of claim 12 wherein the mineral compound(s) represent(s) from 0.001% to 3% by weight approximately relative to the total weight of the dye composition.

30. The composition of claim 15 wherein the weight ratio of the mineral compound(s) to the 4,5-diamino 1-hydroxyethyl pyrazole and/or the addition salt(s) with an acid is between 0.001 and 10.

* * * * *